United States Patent
Poul et al.

(10) Patent No.: US 10,588,987 B2
(45) Date of Patent: Mar. 17, 2020

(54) COMPOSITIONS AND METHODS FOR USE IN MEDICAL DIAGNOSIS

(71) Applicant: NANOBIOTIX, Paris (FR)

(72) Inventors: Laurence Poul, Paris (FR); Laurent Levy, Paris (FR); Celine Berjaud, Paris (FR); Matthieu Germain, Champigny sur Marne (FR); Agnes Pottier, Paris (FR)

(73) Assignee: NANOBIOTIX, Paris (FR)

( * ) Notice: Subject to any disclaimer, the term of this patent is extended or adjusted under 35 U.S.C. 154(b) by 0 days.

(21) Appl. No.: 14/898,763

(22) PCT Filed: Jun. 19, 2014

(86) PCT No.: PCT/EP2014/062947
§ 371 (c)(1),
(2) Date: Dec. 16, 2015

(87) PCT Pub. No.: WO2014/202723
PCT Pub. Date: Dec. 24, 2014

(65) Prior Publication Data
US 2016/0136303 A1 May 19, 2016

Related U.S. Application Data

(60) Provisional application No. 61/837,389, filed on Jun. 20, 2013.

(30) Foreign Application Priority Data

Jun. 20, 2013 (EP) ..................... 13305831

(51) Int. Cl.
| | | |
|---|---|---|
| A61K 49/04 | (2006.01) | |
| A61K 9/08 | (2006.01) | |
| A61K 9/51 | (2006.01) | |
| A61K 47/50 | (2017.01) | |
| A61K 9/00 | (2006.01) | |
| A61K 9/06 | (2006.01) | |

(52) U.S. Cl.
CPC ............ *A61K 49/04* (2013.01); *A61K 9/0024* (2013.01); *A61K 9/06* (2013.01); *A61K 9/08* (2013.01); *A61K 9/5115* (2013.01); *A61K 47/50* (2017.08); *A61K 49/0423* (2013.01); *A61K 49/0457* (2013.01)

(58) Field of Classification Search
None
See application file for complete search history.

(56) References Cited

U.S. PATENT DOCUMENTS

| | | | |
|---|---|---|---|
| 8,845,507 B2 | 9/2014 | Levy et al. | |
| 2005/0084869 A1* | 4/2005 | Kim | C12Q 1/6886 435/6.11 |
| 2007/0217996 A1* | 9/2007 | Levy | A61K 41/0038 424/1.33 |
| 2011/0142936 A1 | 6/2011 | Campbell et al. | |
| 2011/0223255 A1 | 9/2011 | Thiesen et al. | |
| 2014/0219926 A1* | 8/2014 | Cunkelman | A61K 9/5161 424/9.322 |

FOREIGN PATENT DOCUMENTS

| | | |
|---|---|---|
| DE | 10 2006 041495 | 3/2008 |
| DE | 10 2008 008522 | 8/2009 |
| EP | 2 130 553 | 12/2009 |
| JP | 2003-517453 | 5/2003 |
| JP | 2013-514152 | 4/2013 |
| WO | WO 00/45854 | 8/2000 |
| WO | WO 2013/076305 | 5/2013 |

OTHER PUBLICATIONS

U.S. Appl. No. 61/759,852, filed Feb. 1, 2013.*
Viscosity (https://www.saylor.org/site/wp-content/uploads/2011/04/Viscosity.pdf(downloaded Jul. 23, 2018) (Year: 2018).*
Written Opinion in International Application No. PCT/EP2014/062947, dated Jul. 21, 2014, pp. 1-4.
Ahmad, M. et al. "Synthesis of Silver Nanoparticles in Chitosan, Gelatin and Chitosan/Gelatin Bionanocomposites by a Chemical Reducing Agent and Their Characterization" *Molecules*, 2011, pp. 7237-7248, vol. 16.

* cited by examiner

*Primary Examiner* — Jake M Vu
(74) *Attorney, Agent, or Firm* — Saliwanchik, Lloyd & Eisenschenk

(57) ABSTRACT

The present invention relates to compositions and methods for use in medical diagnosis and patient monitoring. It more particularly relates to a biocompatible gel comprising nanoparticles and/or nanoparticle aggregates, wherein: i) the nanoparticles and/or nanoparticles of said aggregate comprise an inorganic material comprising at least one metal element having an atomic number Z of at least 25, each of said nanoparticles and nanoparticle aggregates being covered with a biocompatible coating; ii) the nanoparticles' and/or nanoparticle aggregates' concentration is of about or less than 0.5% (w/w); and iii) the apparent viscosity at 2 s$^{-1}$ of the gel comprising the nanoparticles and/or nanoparticle aggregates is between about 0.1 Pa·s and about 1000 Pa·s when measured between 20° C. and 37° C. The composition of the invention typically allows the delineation and visualization of at least 40% of the target biological tissue when said tissue is observed using an X-ray imaging equipment.

11 Claims, 4 Drawing Sheets

COMPOSITIONS AND METHODS FOR USE IN MEDICAL DIAGNOSIS

CROSS-REFERENCE TO RELATED APPLICATIONS

This application is the U.S. national stage application of International Patent Application No. PCT/EP2014/062947, filed Jun. 19, 2014, which claims the benefit of U.S. Provisional Patent Application No. 61/837,389, filed Jun. 20, 2013.

FIELD OF THE INVENTION

The invention relates to compositions and methods for use in medical diagnosis and patient monitoring. It more particularly relates to a biocompatible gel comprising nanoparticles and/or nanoparticle aggregates, typically for use for delineating, and preferably also visualizing, at least 40% of a target biological tissue when the target biological tissue is observed using X-ray imaging equipment, wherein: i) the nanoparticles and/or nanoparticles of said nanoparticle aggregate comprise an inorganic material comprising at least one metal element having an atomic number Z of at least 25, each of said nanoparticles and nanoparticle aggregates being covered with a biocompatible coating; ii) the nanoparticles' and/or nanoparticle aggregates' concentration is of about or less than 0.5% (w/w); and iii) the apparent viscosity at $2\ s^{-1}$ of the gel comprising the nanoparticles and/or nanoparticle aggregates is between about 0.1 Pa·s and about 1000 Pa·s when measured between 20° C. and 37° C.

The composition of the invention typically allows the delineation and visualization of at least 40%, preferably at least 50% and even more preferably more than 50%, of the target biological tissue when said tissue is observed using X-ray imaging equipment.

BACKGROUND

The local control of cancer's recurrence or relapse constitutes a crucial step of anti-cancer treatment following surgery and radiotherapy steps. Post-operative radiotherapy is used in several indications to treat the tumor bed once tumorectomy has been performed in order to improve rates of local control and thus reduce, and ideally avoid, tumor recurrences. A recent meta-analysis of the Early Breast Cancer Trialists' Collaborative Group stressed the importance of reducing local breast tumor recurrences, because one breast cancer death could be avoided for every four local recurrences avoided. According to the authors of "*Customized computed tomography-based boost volumes in breast-conserving therapy: use of three-dimensional histologic information for clinical target volume margins*" [IJROBP, 75(3): 757-763 (2009)], one method to improve local control is to increase the radiation dose the tumor bed is exposed to (i.e., boost irradiation). The authors add that this effect could be further increased by improving the delineation of the tumor bed (i.e., the target volume the boost irradiation should specifically target).

The International Commission on Radiation Units and Measurements defines the Gross Tumor Volume (GTV) as the gross demonstrable extent and location of a malignant growth. For the adjuvant breast radiotherapy (the surgical step is followed by a radiotherapy step), the GTV has been excised with a variable margin of tissue, leaving a cavity. The cavity is not the GTV, but related to it. The cavity walls are referred to, somewhat loosely, as the tumor bed ["*Target volume definition for external beam partial breast radiotherapy: clinical, pathological and technical studies informing current approaches*," Radiotherapy and Oncology, 94: 255-263 (2010)].

In clinical practice, accurately identifying the tumor bed is challenging and a high rate of inter-observer variability in tumor bed contouring is frequently reported, especially in poorly visualized resection cavities ["*Excised and Irradiated Volumes in Relation to the Tumor size in Breast-Conserving Therapy*," Breast Cancer Res. Treat., 129:857-865 (2011)]. The irradiated postoperative volume (as delineated on the radiotherapy planning CT scan before the start of radiotherapy) in patients treated with breast-conserving therapy is not, for most of the cases, clearly visible and a cavity visualization score is frequently used to assess the quality of the irradiated postoperative volume identification.

Likewise, for prostate cancers, the EORTC Radiation Oncology Group has made recommendations for target volume definition in post-operative radiotherapy, presenting guidelines for standardization of the target volume definition and delineation as well as standardization of the clinical quality assurance procedures; the authors of "*Guidelines for target volume definition in post-operative radiotherapy for prostate cancer, on behalf of the EORTC Radiation Oncology Group*" [Radiotherapy & Oncology, 84: 121-127 (2007)] in particular referred to a study where a high inter-observer variability of target volume delineation in postoperative radiotherapy for prostate cancer was observed when performed by five (5) distinct radiation oncologists for eight (8) distinct patients. (The CTV varied between the physicians from 39 to 53 $cm^3$ for the patient corresponding to the smallest variation and from 16 to 69 $cm^3$ for the patient corresponding to the largest variation.)

A study to evaluate the accuracy of a boost technique, reported in "*Improving the definition of the tumor bed boost with the use of surgical clips and image registration in breast cancer patients*" [Int. J. Radiation Oncology Biol. Phys., 78(5): 1352-1355 (2010)], shows that the use of radiopaque clips during tumorectomy, typically 3 or more clips, increases the accuracy of the tumor bed delineation (see FIG. 1). However, questions of the accuracy of CT/clip-based TB delineation remain. Clips only define points located on the excision cavity walls such that the remaining tumor tissue-excision cavity interface must be derived by interpolation, taking into account tissue density and distortion.

Interestingly, a report on the magnitude of volumetric change in the post-lumpectomy tumor bed has demonstrated significant tumor bed volume changes before and during radiation therapy or radiotherapy (RT) ["*The dynamic tumor bed: volumetric changes in the lumpectomy cavity during breast conserving therapy*" Int. J. Radiation Oncology Biol. Phys., 74(3):695-701 (2009)]. Thirty-six (36) patients were enrolled in the study, with Tis (10), T1 (24) and T2 (2) breast tumors. Thirty (30) patients received a whole breast irradiation after lumpectomy followed by a boost dose of 10 Gy. Six (6) patients were treated with partial breast irradiation. Treatment planning CT scans of the breast were obtained shortly after surgery, before the start of the whole breast irradiation for treatment planning and before delivery of the tumor bed boost. Patients who were treated with partial breast irradiation received only a scan postoperatively and a scan before tumor bed treatment.

During the interval between the postoperative scan and second scan (median interval, 3 weeks), the tumor bed volume decreased by a median of 49.9%. Between the planning scan and the boost scan (median interval, 7 weeks), the median tumor bed volume decreased by 44.6%.

A subgroup of eight (8) patients, who experienced a delay (median interval, 23 weeks) between surgery and RT because of planned chemotherapy, had a median reduction of the tumor bed volume of 60.3% during the interval between the postoperative scan and planning scan. When this magnitude and rate-of-change data were evaluated in the context of the entire patient set, the observed results suggested that the tumor bed volume decreased more rapidly in the weeks immediately after surgery and then attained a relative plateau.

According to the authors, the impact of large volumetric change on planning volume, dosimetry, or clinical parameters such as local control or cosmetic outcome is an important area for future research, as theoretically, if a single planning scan is used to plan the boost clinical target volume (CTV) in a patient with a tumor bed that shrinks dramatically during the course of RT, the surrounding normal tissues receive unnecessary additional radiation that could yield poorer cosmetic outcomes and more late undesirable effects. Conversely, if a single planning scan is performed long after surgery, the reduced tumor bed volume could actually result in underestimating the true tumor bed or the area of surgical tumor contamination.

WO 2011/084465 relates to stabilizing and visualizing tissue gaps left by surgical removal of cancerous tissues. According to the inventors, a conformal filling approach is a considerable improvement over the use of clips, which provide poor resolution of the site's margins. The described implants may be formulated to be stable until no longer needed, and then biodegrade. According to WO 2011/084465, the implantation of the hydrogel leads to an increase of the mean cavity volume. Therefore, when using standard margins, the hydrogel tends to increase normal tissue radiation doses. A reduced margin expansion is thus required in order to decrease normal tissue radiation doses.

As easily understandable from the above, there remains a clear need to improve the post-surgery tumor bed delineation.

DETAILED DESCRIPTION

The inventors now provide an advantageous composition which considerably improves targeted tissue delineation, in particular tumor bed delineation, without impacting targeted tissue volume changes, typically when considering a tumor bed, tumor bed volumes changes or post-lumpectomy tissue remodeling. In the context of the invention, the tumor bed is the tissue covering the cavity obtained following tumor resection.

A first object relates to a biocompatible gel comprising nanoparticles and/or nanoparticle aggregates, typically for use for delineating, and preferably also visualizing, at least 40% of a target biological tissue when the target biological tissue is observed using X-ray imaging equipment, wherein: i) the nanoparticles and/or nanoparticles of said aggregate comprise an inorganic material comprising at least one metal element having an atomic number Z of at least 25, each of said nanoparticles and said nanoparticle aggregates being covered with a biocompatible coating; ii) the nanoparticles' and/or nanoparticle aggregates' concentration is of about or less than 0.5% (w/w); and iii) the apparent viscosity at 2 s$^{-1}$ of the gel comprising nanoparticles and/or nanoparticle aggregates is between about 0.1 Pa·s and about 1000 Pa·s when measured between 20° C. and 37° C.

The biocompatible gel comprising nanoparticles and/or nanoparticle aggregates according to the invention advantageously allows the delineation and visualization of at least 40%, preferably at least 50%, even more preferably more than 50%, of a target biological tissue when the target biological tissue is observed using X-ray imaging equipment.

The targeted biological tissue is typically a tumor bed.

Inorganic Nanoparticles

In the present description, the terms "nanoparticle(s)", "nanoparticle aggregate(s)" and "particle(s)" are indifferently used.

In the context of the present invention, the terms "nanoparticle" or "nanoparticle aggregate" refer to a product, in particular a synthetic product, with a size in the nanometer range, typically between 1 nm and 500 nm.

The size of the nanoparticle and its structure and composition may be analyzed from an X-ray diffractogram.

The terms "aggregate of nanoparticles" or "nanoparticle aggregate" refer to an assemblage of nanoparticles strongly, typically covalently, bound to each other.

The terms "size of the nanoparticle" or "size of the nanoparticle aggregate" and "largest size of the nanoparticle" or "largest size of the nanoparticle aggregate" herein refer to the "largest dimension of the nanoparticle", "largest dimension of the nanoparticle aggregate", "diameter of the nanoparticle" or "diameter of the nanoparticle aggregate".

Transmission Electron Microscopy (TEM) can be used to measure the size of the nanoparticle or nanoparticle aggregate. Also, Dynamic Light Scattering (DLS) can be used to measure the hydrodynamic diameter of nanoparticles or nanoparticle aggregates in solution. These two methods may further be used one after the other to compare size measurements and confirm said size.

The largest dimension of a nanoparticle or nanoparticle aggregate as herein defined is typically between about 5 nm and about 250 nm, preferably between about 10 nm and about 100 nm or about 200 nm, even more preferably between about 20 nm and about 150 nm.

As the shape of the particle can influence its "biocompatibility", particles having a quite homogeneous shape are preferred. For pharmacokinetic reasons, nanoparticles or nanoparticle aggregates that are essentially spherical, round or ovoid in shape are thus preferred. Such a shape also favors the nanoparticle or nanoparticle aggregate's interaction with or uptake by cells. Spherical or round shape is particularly preferred.

Typically, the largest dimension is the diameter of a nanoparticle or nanoparticle aggregate of round or spherical shape, or the longest length of a nanoparticle or nanoparticle aggregate of ovoid or oval shape.

The inorganic material the nanoparticle or nanoparticle aggregate is prepared with typically comprises at least one metal element, typically a metal element having an atomic number Z of at least 25. The inorganic material can also comprise several metal elements, typically two metal elements.

In a particular embodiment the nanoparticle or nanoparticle aggregate consists of an inorganic material, said inorganic material comprising a single metal element or a mixture of metal elements.

The inorganic material is preferably a material having an effective atomic number ($Z_{eff}$) of at least 25, preferably at least 40 or 41, more preferably at least 50 or 51, more preferably at least 60, 61, 62 or even 63.

Effective atomic number is a term that is similar to atomic number but is used for compounds (e.g., water) and mixtures of different materials (such as tissue and bone) rather than for atoms. Effective atomic number calculates the average atomic number for a compound or mixture of materials. It is abbreviated $Z_{eff}$.

The effective atomic number is calculated by taking the fractional proportion of each atom in the compound and multiplying that by the atomic number of the atom. The formula for the effective atomic number, $Z_{eff}$, is as follows:

$$Z_{eff} = \sqrt[2.94]{f_1 \times (Z_1)^{2.94} + f_2 \times (Z_2)^{2.94} + f_3 \times (Z_3)^{2.94} + \ldots}$$

where $f_n$ is the fraction of the total number of electrons associated with each element, and $Z_n$ is the atomic number of each element.

The atomic number (also known as the proton number) is the number of protons found in the nucleus of an atom. It is traditionally represented by the symbol Z (and is herein also identified as $Z_n$). The atomic number uniquely identifies a chemical element. In an atom of neutral charge, atomic number is equal to the number of electrons.

An example is that of water ($H_2O$) which is made up of two hydrogen atoms (Z=1) and one oxygen atom (Z=8). The total number of electrons is 1+1+8=10. The fraction of electrons corresponding to the two hydrogens is 2/10 and the fraction of electrons corresponding to the unique oxygen is (8/10). $Z_{eff}$ of water is therefore:

$$Z_{eff} = \sqrt[2.94]{0.2 \times 1^{2.94} + 0.8 \times 8^{2.94}} = 7.42$$

$Z_{eff}$ participate to the incoming radiations absorption capacity of nanoparticles.

The inorganic material constituting the nanoparticle and/or nanoparticle aggregate is typically selected from a metal, an oxide, a sulfide and any mixture thereof. Typically this inorganic material comprises at least one metal element having an atomic number Z of at least 25.

When the inorganic material constituting the nanoparticle and/or nanoparticle aggregate is an oxide, this oxide may be selected for example from iron oxide ($Fe_3O_4$ or $Fe_2O_3$), zirconium oxide ($ZrO_2$), cerium (IV) oxide ($CeO_2$), neodynium (III) oxide ($Nd_2O_3$), samarium (III) oxide ($Sm_2O_3$), europium (III) oxide ($Eu_2O_3$), gadolinium (III) oxide ($Gd_2O_3$), terbium (III) oxide ($Tb_2O_3$), dysprosium (III) oxide ($Dy_2O_3$), holmium oxide ($Ho_2O_3$), erbium oxide ($Er_2O_3$), thulium (III) oxide ($Tm_2O_3$), ytterbium oxide ($Yb_2O_3$), lutetium oxide ($lu_2O_3$), hafnium (IV) oxide ($HfO_2$), tantalum (V) oxide ($Ta_2O_5$), rhenium (IV) oxide ($ReO_2$), and bismuth (III) oxide ($Bi_2O_3$).

In a particular embodiment, a mixture of oxides can also be used as the inorganic material to prepare the nanoparticle and/or nanoparticle aggregate of the invention. The nanoparticle and/or nanoparticle aggregate of the invention can thus comprise or consist of a mixture of oxides.

When the inorganic material constituting the nanoparticle and/or nanoparticle aggregate is a metal, this metal may be selected for example from gold metal (Au), silver metal (Ag), platinum metal (Pt), palladium metal (Pd), tin metal (Sn), tantalum metal (Ta), ytterbium metal (Yb), zirconium metal (Zr), hafnium metal (Hf), terbium metal (Tb), thulium metal (Tm), cerium metal (Ce), dysprosium metal (Dy), erbium metal (Er), europium metal (Eu), holmium metal (Ho), iron metal (Fe), lanthanum metal (La), neodymium metal (Nd), praseodymium metal (Pr), and lutetium metal (Lu). As indicated previously, in a particular embodiment, a mixture of metals can also be used as the inorganic material to prepare the nanoparticle and/or nanoparticle aggregate of the invention.

The nanoparticle and/or nanoparticle aggregate of the invention can thus comprise or consist of a mixture of metals.

When the inorganic material constituting the nanoparticle and/or nanoparticle aggregate is a sulfide, this sulfide may be selected for example from silver sulfide ($Ag_2S$), bismuth sulfide ($Bi_2S_3$), and iron sulfide ($Fe_3S_4$). In a particular embodiment, a mixture of sulfides can also be used to prepare the nanoparticle and/or nanoparticle aggregate of the invention. The nanoparticle and/or nnanoparticle aggregate of the invention can thus comprise or consist of a mixture of sulfides.

A mixture of an oxide, a metal and/or a sulfide can also be used to prepare the nanoparticles and/or nanoparticle aggregates of the invention. The nanoparticle and/or nanoparticle aggregate of the invention can thus comprise or consist of a mixture of an oxide, a metal and/or a sulfide.

An example of a nanoparticle which can advantageously be used in the context of the present invention is a gold metal nanoparticle covered with hafnium oxide material.

In a preferred embodiment, the nanoparticle and/or nanoparticle aggregate used in the context of the present invention can be coated with a biocompatible material selected from an agent displaying a steric group. Such a group may be selected for example from polyethyleneglycol (PEG); polyethylenoxide; polyvinylalcohol; polyacrylate; polyacrylamide (poly(N-isopropylacrylamide)); polycarbamide; a biopolymer; a polysaccharide such as dextran, xylan and cellulose; collagen; and a zwitterionic compound such as polysulfobetain, etc.

In another preferred embodiment, the nanoparticle and/or nanoparticle aggregate can be coated with a biocompatible material selected from an agent allowing interaction with a biological target. Such an agent can typically bring a positive or negative charge on the nanoparticle's surface. This charge can be determined by zeta potential measurements, typically performed on nanoparticles and/or nanoparticle aggregate suspensions the concentration of which vary between 0.2 and 10 g/L, the nanoparticles and/or nanoparticle aggregates being suspended in an aqueous medium with a pH comprised between 6 and 8.

An agent forming a positive charge on the nanoparticle surface can be for example aminopropyltriethoxysilane or polylysine. An agent forming a negative charge on the nanoparticle surface can be for example a phosphate (for example a polyphosphate, a metaphosphate, a pyrophosphate, etc.), a carboxylate (for example citrate or dicarboxylic acid, in particular succinic acid) or a sulfate.

Advantageously, the coating preserves the integrity of the nanoparticle and/or nanoparticle aggregate in vivo, ensures or improves the biocompatibility thereof, and facilitates an optional functionalization thereof (for example with spacer molecules, biocompatible polymers, targeting agents, proteins, etc.).

A particular nanoparticle and/or nanoparticle aggregate according to the present invention can further comprise at least one targeting agent allowing its interaction with a recognition element present on the target cell. Such a targeting agent typically acts once the nanoparticles and/or nanoparticle aggregates delineate the target site. The targeting agent can be any biological or chemical structure displaying affinity for molecules present in the human or animal body. For instance it can be a peptide, oligopeptide or polypeptide, a protein, a nucleic acid (DNA, RNA, SiRNA, tRNA, miRNA, etc.), a hormone, a vitamin, an enzyme, or the ligand of a molecule expressed by a pathological cell, in particular the ligand of a tumor antigen, hormone receptor, cytokine receptor or growth factor receptor. Said targeting agents can be selected for example from the group consisting of LHRH, EGF, a folate, anti-B-FN antibody, E-selectin/P-selectin, anti-IL-2Rα antibody, GHRH, etc.

Biocompatible Gel

A natural polymer gel is mainly obtained by the formation of intermolecular bonds as a result of i) temperature and pH changes and ii) the presence of metallic ions. Thus, during the formation of the gel, a reversible solution-gel transition takes place.

On the other hand, synthetic gels consist of polymer chains connected by covalent bonds or other physical bonds. These structures typically lead to irreversible gel formation.

The properties of gels are influenced by both networks and solvents. A gel swells when immersed in a good solvent. Hydrogels are gels that typically swell in aqueous environments.

A preferred biocompatible gel according to the invention is a biocompatible hydrogel.

Polymers used for medical applications are to be biocompatible; i.e., upon contact with a body, for example with internal organs or with any other biological systems, they should not cause inflammation and/or adverse reactions.

Typical polymers which can be used to form the biocompatible gel can be selected from polyethylenimine (PEI); polyethyleneglycol (PEG); polypropyleneglycol (PPG); polysaccharide, including for example cellulose derivatives (for example methylcellulose, carboxymethylcellulose, hydroxyethylcellulose, and hydroxypropylcellulose), hyaluronic acid derivatives, chitosan, dextran, etc.; poly (acrylamide) derivatives; poly(lactic acid) (PLA) derivatives; poly(acrylic acid) (PAA) derivatives; poly(lactide-co-glycolic) acid (PLGA) derivatives; polyvinylalcohol (PVA); poly(vinylpyrrolidone); polyalkylcyanoacrylate derivatives; collagen derivatives; poly(glutamic acid) (PGA); and gelatin. The biocompatible gel can also be composed of any mixture of the herein-identified polymers.

Preferred polymers which can be advantageously used to prepare biocompatible hydrogels can be selected from the polysaccharide family which includes i) cellulose derivatives, typically methylcellulose, carboxymethylcellulose, hydroxyethylcellulose, and hydroxypropylcellulose, and ii) members of the hyaluronic acid family or derivatives thereof.

The quantity of polymer to be dispersed in a solvent in order to form a biocompatible gel according to the invention is typically between 0.1% and 50% (weight by weight w/w), more preferably between 0.5% and 40%, typically between 0.5% and 35%, or between 0.5% and 25%, and even more preferably between about 1%, about 2%, or about 3% and about 15% or about 20% (w/w).

When the biocompatible gel is a hydrogel, the solvent is typically an aqueous medium.

The apparent viscosity at $2\ s^{-1}$ of the biocompatible gel comprising nanoparticles and/or nanoparticle aggregates, for a temperature between 20° C. and 37° C., is between about 0.1 Pa·s and about 1000 Pa·s, preferably between 1 Pa·s and 750 Pa·s, typically between 5 Pa·s and 500 Pa·s or 5 Pa·s and 300 Pa·s. Viscosity measurement is typically performed, at 20° C. and 37° C., using a Couette rheometer (MODEL RM200, LAMY Rheology) at a given range of shear rate, lying between $0.1\ s^{-1}$ and $300\ s^{-1}$. The apparent viscosity is reported at $2\ s^{-1}$.

For each sample, the measurement is carried out on a volume of at least 25 ml with the suitable spindle, following the standard DIN ISO 3219 recommendations.

Particle/Gel Interaction

In the biocompatible gel comprising nanoparticles and/or nanoparticle aggregates according to the invention, each nanoparticle or nanoparticle aggregate comprises or consists of an inorganic material, typically an inorganic material comprising at least one metal element having an atomic number Z of at least 25, and each nanoparticle or nanoparticle aggregate is advantageously covered with a biocompatible coating.

The nanoparticles' and/or nanoparticle aggregates' concentration within the gel is of about or less than 0.5% (w/w). In a preferred embodiment, the nanoparticles' and/or nanoparticle aggregates' concentration within the gel is between about 0.15% and 0.5% (w/w), typically between 0.2% and 0.5% (w/w). For example, the nanoparticles' and/or nanoparticle aggregates' concentration within the gel is equal to about 0.2%, 0.4% or 0.5% (w/w).

The absence of any strong interaction (a strong interaction being typically a covalent interaction) between the nanoparticles and/or nanoparticle aggregates and the polymer which forms the biocompatible gel is an important feature to ensure that said nanoparticles and/or nanoparticle aggregates are actually released from the gel in order for them to correctly delineate the tumor bed.

The absence of strong interaction between the particle and the polymer which forms the biocompatible gel can typically be verified by measuring the viscosity of the gel comprising the nanoparticles and/or nanoparticle aggregates at 20° C. and 37° C., as described above, and by comparing the obtained viscosity curve with that of a gel comprising neither nanoparticles nor nanoparticle aggregates. Similar viscosity curves (i.e., values differing from each other by no more than 20%, typically by no more than 15%) confirm the absence of strong interaction between nanoparticles and/or nanoparticle aggregates and gel.

Biological Tissues and Tumor Bed Delineation and Visualization

The biocompatible gel of the invention can be used in many fields, particularly in human or veterinary medicine. The biocompatible gel according to the invention, as herein described, is preferably for use in a mammal, even more preferably in a human being, to delineate, typically delineate and visualize, a targeted tissue, in particular to delineate and visualize a tumor bed, preferably while using X-ray imaging equipment, such as a CT scanner.

Classically used methods for tumor bed visualization and treatment planning (i.e., planning of the appropriate radiotherapy) include clinical methods such as: i) planning the palpation and/or the surgical scar; ii) planning taking into account pre-surgical imaging findings (typically mammography), clinical history and/or operative report; and iii) planning typically including radiography, computed tomography (CT), positron emission tomography (PET), or magnetic resonance imaging (MM), as known by the skilled person.

Medical imaging technologies using X-rays, such as CT scanners, are commonly used technologies to determine tumor bed treatment planning.

Computed tomography (CT) imaging is based on the variable absorption of X-rays by different tissues, and provides a cross-sectional imaging. The term "tomography" derives from the Greek term "tomos" meaning "slice" or "section" and "graphy" meaning "drawing". A CT imaging system produces cross-sectional images of the bones and soft tissues inside the body. CT images can be combined to create 3D images.

The nanoparticles and/or nanoparticle aggregates used in the context of the present invention comprise or consist of an inorganic material preferably comprising at least one metal element with an atomic number of at least 25. The nanoparticles are intrinsically radio-opaque (i.e., they absorb X-rays) and can be easily visualized, typically through radiography or computed tomography.

When exposed to X-rays, typically delivered by CT scanner, the nanoparticles and/or nanoparticle aggregates create a marked contrast in the CT images due to the difference of electron density of the target biological tissues and the particles.

The Hounsfield number is a normalized value of the calculated X-ray absorption coefficient of a pixel (picture element) in a computed tomogram. This number is expressed in Hounsfield units (HU). The CT number of air is $-1000$ (HU=$-1000$) and that of water is 0 (HU=0). For inorganic particles with a high $Z_{eff}$, separation between tissues and particles occurs typically around HU values of 150. Above HU values of typically 120 up to 200, no more soft tissue densities can be measured.

The biocompatible gel comprising the nanoparticles and/or nanoparticle aggregates of the invention can be administered to the subject i) by deposition on the biological tissue of interest (targeted tissue) or ii) by filling the cavity left typically after a tumorectomy, preferably at the time of surgery (tumor resection).

Nanoparticles or aggregates of nanoparticles release from the gel and then deposit on the targeted tissue, preferably on a tumor bed.

Preferably, the nanoparticles or aggregates of nanoparticles deposit on the targeted tissue typically between 24 hours and less than 1 month, preferably between 24 hours and 3 weeks, more preferably between 24 hours and 2 weeks, in order to allow for perfect and persistent targeted tissue delineation. Such delineation will be of high value, typically in the context of any further treatment planning.

When a cavity is to be filled with a gel according to the invention, the gel may fill at least 10% of the cavity's volume, preferably 20% of the cavity's volume, even more preferably more than 30%, 40%, 50%, 60%, 70%, 80%, or 90% of the cavity's volume. 100% of the cavity's volume can also be filled with such a gel.

Repeated administrations of the gel can be performed, when appropriate.

The delineation of the targeted tissue allowed by the gel according to the present invention which comprises nanoparticles and/or aggregates of nanoparticles can be visualized typically using X-ray medical imaging equipment, and more preferably a CT scanner. The term "delineate" means that the nanoparticles or aggregates of nanoparticles: i) cover at least about 40%, preferably at least about 50%, and even more preferably more than about 50%, 60%, 70%, 80%, 90%, or about 95% of the targeted tissue; and preferably ii) form on the surface of the targeted tissues a layer with a thickness comprised between 100 µm and 0.5 cm, for example between 500 µm and 0.5 cm. The Hounsfield (HU) number within the layer is of at least 120 HU. Ideally, the nanoparticles or aggregates of nanoparticles cover 99% or even 100% of the targeted tissues.

Also herein described is a method of delineating a tumor bed in a subject, such a delineation allowing the subsequent visualization of said tumor bed using X-ray imaging equipment, wherein said method comprises exposing the tumor bed of a subject to a biocompatible gel comprising the nanoparticles or nanoparticle aggregates according to the invention (as herein described), typically through deposition of the gel into the tumor bed, preferably at the time of surgery (tumor resection), in order to obtain the delineation of the tumor bed with a delay comprised between 24 hours and less than 1 month, preferably between 24 hours and 3 weeks, more preferably between 24 hours and 2 weeks following deposition. The tumor bed delineation can then be visualized by using X-ray imaging equipment.

The invention can be used to delineate any tumor bed of any type of malignant solid tumors, in particular of epithelial, neuroectodermal or mesenchymal origin, as well as lymphatic cancers so long as lymphatic nodes are concerned.

The biocompatible gel comprising the nanoparticles and/or aggregates of nanoparticles herein described is in particular intended to be used in the context of a cancer treatment protocol where radiotherapy is a classical adjuvant treatment or is the most appropriate adjuvant treatment for a particular subject, or where radiotherapy could be indicated as adjuvant treatment. Such cancer may be selected in particular from the group consisting of skin cancer, including malignant neoplasms associated with AIDS; melanoma; squamous cancer; central nervous system tumors including brain, cerebellum, pituitary, spinal cord, brainstem, eye and orbit; head and neck tumors; lung cancers; breast cancers; gastrointestinal tumors such as liver and hepatobiliary tract cancers, colon, rectum and anal cancers, and stomach, pancreatic, and esophageal cancers; male genitourinary tumors such as prostate, testicular, penile and urethral cancers; gynecological tumors such as uterine cervical, endometrial, ovarian, fallopian tube, vaginal and vulvar cancers; adrenal and retroperitoneal tumors; sarcomas of bone and soft tissue regardless the localization; and pediatric tumors such as Wilm's tumor, neuroblastoma, central nervous system tumors, Ewing's sarcoma, etc.

A further object of the invention relates to a kit comprising a biocompatible gel comprising nanoparticles and/or nanoparticle aggregates according to the present invention (as herein described), optionally together with a therapeutic agent. In a particular embodiment, the kit comprises, in distinct containers, a biocompatible gel as herein described and a suspension of nanoparticles or nanoparticle aggregates as herein described (which are intended to be contacted, typically mixed, either in situ, i.e., on the target site, or ex vivo before deposition of the mixture on the target site).

A kit comprising a biocompatible gel comprising nanoparticles and/or nanoparticle aggregates as herein described, wherein the biocompatible gel and the nanoparticles and/or nanoparticle aggregates are in distinct containers, is thus herein further described.

The following examples illustrate the invention without limiting its scope.

From "*Improving the definition of the tumor bed boost with the use of surgical clips and image registration in breast cancer patients*" [*Int. J. Radiation Oncology Biol. Phys.*, 78(5): 1352-1355 (2010)]. Tumor bed volume delineation: gross tumor volume (GTV) (red); clinical target volume (CTV) clips=all clips with 0.5-cm margins; planning target volume (PTV) (green)=GTV+CTV clips+0.5-cm lateral and 1-cm superior-inferior margins.

Figure 1:
FIG. 1: Tumor tissue delineation using clips
Figure 2:
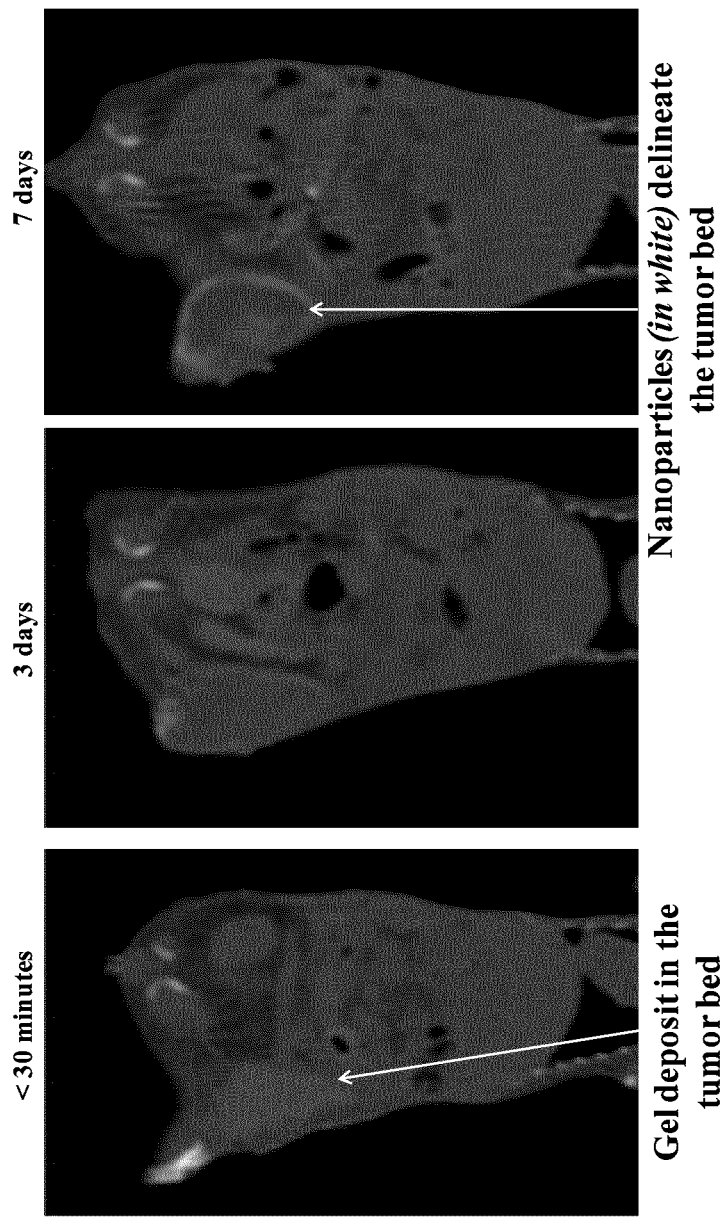

FIG. 2: CT images taken 15 minutes (<30 minutes), 3 days, and 7 days after gel deposition into the cavity left following tumorectomy, showing the tumor bed delineation using a biocompatible hydrogel composed of methylcellulose (4% w/w) comprising nanoparticles and/or nanoparticle aggregates (0.4% w/w) consisting of hafnium oxide. The nanoparticles and/or nanoparticle aggregates have been mixed with the gel prior to the gel deposition into the tumor bed.

Figure 3:
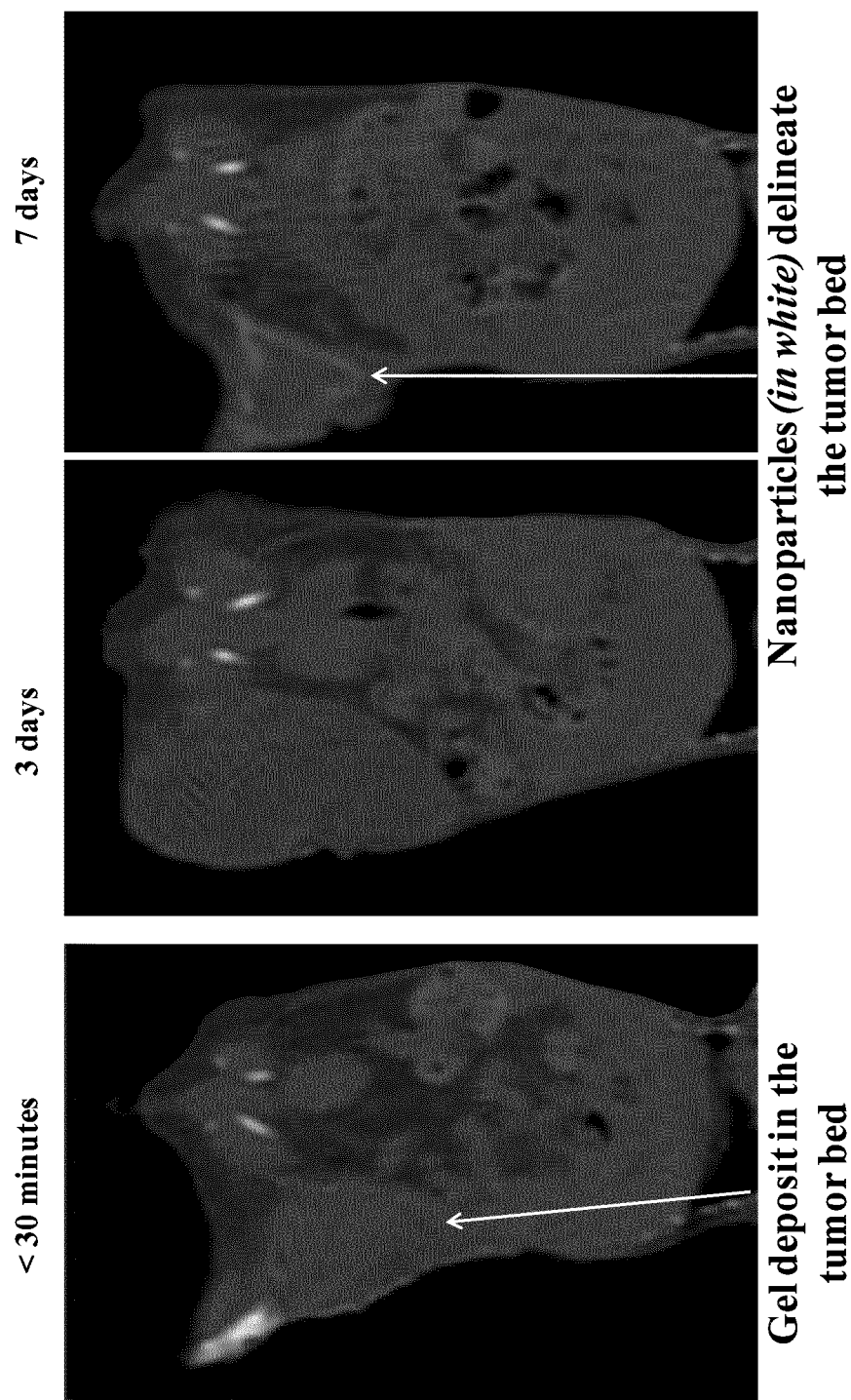

FIG. 3: CT images taken 15 minutes (<30 minutes), 3 days and 7 days after gel deposition into the cavity left following tumorectomy, showing the tumor bed delineation using a biocompatible hydrogel composed of methylcellulose (4% w/w) comprising nanoparticles and/or nanoparticle aggregates (0.2% w/w) consisting of hafnium oxide. The nanoparticles and/or nanoparticle aggregates have been mixed with the gel prior to the gel deposition into the tumor bed.

Figure 4:
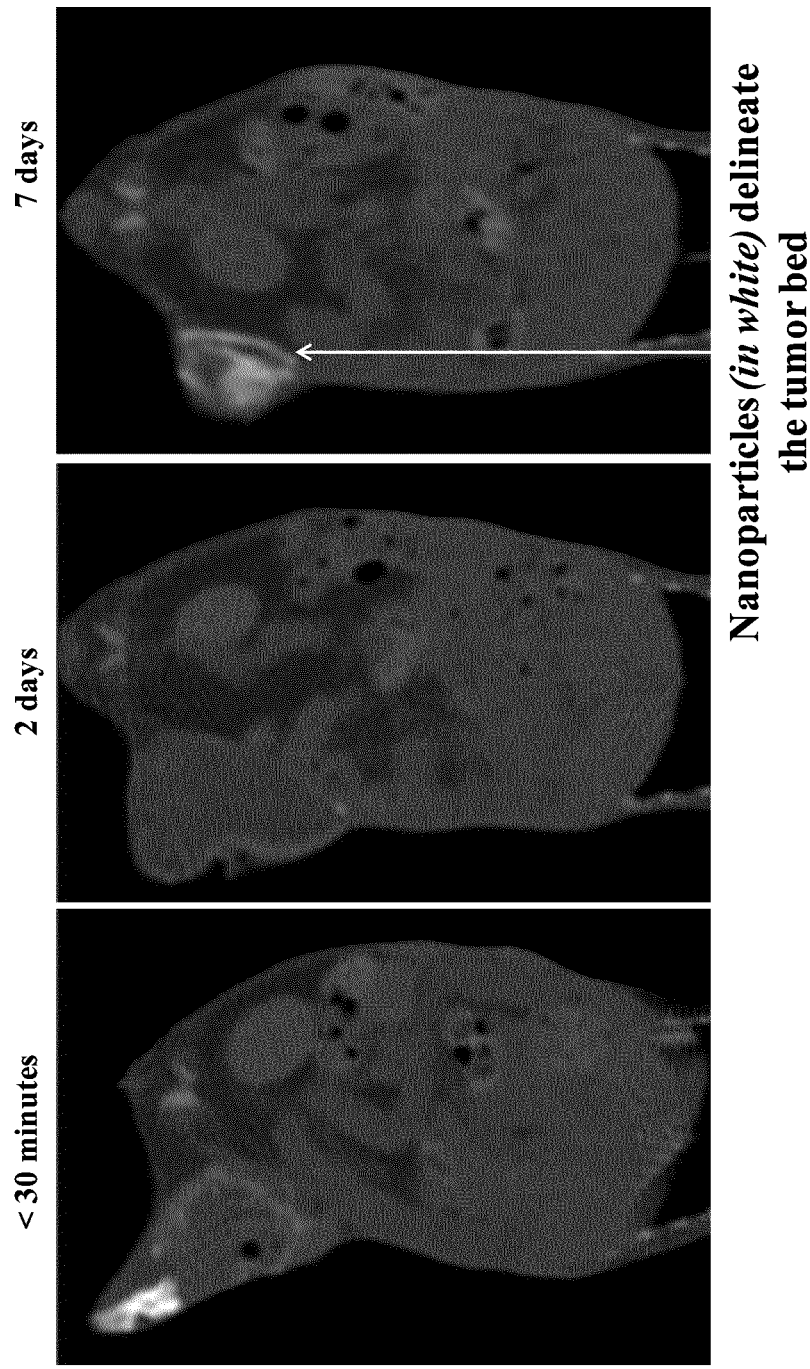

FIG. 4: CT images taken 15 minutes (<30 minutes), 2 days and 7 days after gel deposition into the cavity left following tumorectomy, showing the tumor bed delineation using a biocompatible hydrogel composed of methylcellulose (4% w/w) comprising nanoparticles and/or nanoparticle aggregates (0.4% w/w) consisting of hafnium oxide. The nanoparticles and/or nanoparticle aggregates have been incorporated within the gel at the time of surgery.

EXAMPLES

Example 1: Biocompatible Hafnium Oxide (HfO$_2$) Nanoparticles or Nanoparticle Aggregates, Using Sodium Hexametaphosphate as Coating Agent A tetramethylammonium hydroxide (TMAOH) solution is added to HfCl$_4$ solution. Addition of TMAOH solution is performed until the pH of the final suspension reaches a pH comprised between 7 and 13. A white precipitate is obtained.

The precipitate is further transferred to an autoclave and heated at a temperature comprised between 120° C. and 300° C. to perform crystallization. After cooling, the suspension is washed with de-ionized water.

Sodium hexametaphosphate solution is then added to the washed suspension and the pH is adjusted to a pH comprised between 6 and 8.

Sterilization of the nanoparticle or nanoparticle aggregate suspension is performed prior in vitro or in vivo experiments.

Example 2: Synthesis and Physico-Chemical Characterization of Gold Nanoparticles with Different Sizes Gold nanoparticles are obtained by reduction of gold chloride with sodium citrate in aqueous solution. Protocol was adapted from G. Frens, Nature Physical Science 241 (1973) 21.

In a typical experiment, HAuCl$_4$ solution is heated to boiling. Subsequently, sodium citrate solution is added. The resulting solution is maintained under boiling for an additional period of 5 minutes.

The nanoparticle's size is adjusted from 15 nm up to 105 nm by carefully modifying the citrate versus gold precursor ratio (see Table 1).

The as-prepared gold nanoparticle suspensions are then concentrated using an ultrafiltration device with a 30 kDa cellulose membrane.

The resulting suspensions are ultimately filtered through a 0.22 μm cutoff membrane filter under a laminar hood and stored at 4° C.

Particle size is determined on more than 200 particles, by using Transmission Electronic Microscopy (TEM) and by considering the longest nanoparticle dimension of each particle.

TABLE 1

| Samples | Particle size (nm) | Synthesis Citrate | HAuCl$_4$ |
|---|---|---|---|
| Gold-15 | 15 ± 2 (1σ) | 20 mL 30 mM | 500 mL 0.25 mM |
| Gold-30 | 32 ± 10 (1σ) | 7.5 mL 40 mM | 500 mL 0.25 mM |
| Gold-60 | 60 ± 10 (1σ) | 2 mL 85 mM | 500 mL 0.25 mM |
| Gold-80 | 80 ± 10 (1σ) | 1.2 mL 43 mM | 200 mL 0.30 mM |
| Gold-105 | 105 ± 25 (1σ) | 1.2 mL 39 mM | 200 mL 0.33 mM |

Example 3: Biocompatible Hafnium Oxide Nanoparticles' and/or Nanoparticle Aggregates' Incorporation (0.4% w/w) within the Gel Prior to Gel Deposition on the Tumor Bed A volume of aqueous suspension of biocompatible HfO$_2$ nanoparticles from example 1 is added to a volume of gel, typically with a polymer (methylcellulose) concentration lying between 3.5% w/w and 4.5 w/w. The volume ratio between the suspension of HfO$_2$ nanoparticles and the gel being adjusted to reach a final HfO$_2$ nanoparticle concentration within the gel of 0.4% (w/w). The preparation thus obtained is gently mixed, typically with a magnetic stirrer or a spatula.

Example 4: Biocompatible Hafnium Oxide Nanoparticles' and/or Nanoparticle Aggregates' Incorporation (0.2% w/w) within the Gel Prior to Gel Deposition on the Tumor Bed A volume of aqueous suspension of biocompatible HfO$_2$ nanoparticles from example 1 is added to a volume of gel, typically with a polymer (methylcellulose) concentration lying between 3.5% w/w and 4.5 w/w. The volume ratio between the suspension of HfO$_2$ nanoparticles and the gel being adjusted to reach a final HfO$_2$ nanoparticle concentration within the gel of 0.2% (w/w). The preparation thus obtained is gently mixed, typically with a magnetic stirrer or a spatula.

Example 5: Assessment by Computed Tomography (CT) of the Quality of the "Tumor Bed" Delineation Obtained when Using Nanoparticles Embedded in Hydrogel from Example 3

The objective of this experiment was to assess, by CT (Computed Tomography), the quality of "tumor bed" delineation by nanoparticles (NPs).

The test gel from example 3 was implanted (deposited) into the cavity left by the resection of an EMT-6 ectopic grafted tumor (breast tumor cells) in BALB/cJRj mice.

The CT analysis was performed 15 minutes (<30 minutes), 3 days and 7 days following gel implantation into the cavity left by the resection of the tumor in order to evaluate the volume occupied by the nanoparticles and/or nanoparticle aggregates in the tumor bed over time. For this, a manual segmentation (region of interest (ROI)) was performed around the surgical cavity. Then a thresholding above 120 HU was performed inside the surgical cavity in order to evaluate the presence of nanoparticles or nanoparticle aggregates and to assess both the location and volume occupied by those nanoparticles or nanoparticle aggregates for all mice. FIG. 2 presents the CT images showing more than 50% of cavity delineation as soon as 7 days following surgery and gel implantation.

Example 6: Assessment by Computed Tomography (CT) of the Quality of the "Tumor Bed" Delineation Obtained when Using Nanoparticles Embedded in Hydrogel from Example 4

The objective of this experiment was to assess, by CT (Computed Tomography), the quality of "tumor bed" delineation by nanoparticles (NPs).

The test gel from example 4 was implanted (deposited) into the cavity left by the resection of an EMT-6 ectopic grafted tumor (breast tumor cells) in BALB/cJRj mice.

The CT analysis was performed 15 minutes (<30 minutes), 3 days and 7 days following gel implantation into the cavity left by the resection of the tumor in order to evaluate the volume occupied by the nanoparticles or nanoparticle aggregates in the tumor bed over time. For this, a manual segmentation (region of interest (ROI)) was performed around the surgical cavity. Then a thresholding above 120 HU was performed inside the surgical cavity in order to evaluate the presence of nanoparticles and/or nanoparticle aggregates and to assess both the location and volume occupied by those nanoparticles and/or nanoparticle aggregates for all mice. FIG. 3 presents the CT images showing more than 50% of cavity delineation as soon as 7 days following surgery and gel implantation.

Example 7: GEL Preparation

Gel is formed typically with a polymer (methylcellulose) concentration in water lying between 3.5% w/w and 4.5% w/w. The preparation thus obtained is gently mixed, typically with a magnetic stirrer or a spatula.

Example 8: Assessment by Computed Tomography (CT) of the Quality of the "Tumor Bed" Delineation Obtained when Using Biocompatible Hafnium Oxide Nanoparticles and/or Nanoparticle Aggregates Embedded (0.4% w/w) within the Gel from Example 7, at the Time of Surgery The objective of this study is to assess, by CT (Computed Tomography), the quality of "tumor bed" delineation by nanoparticles (NPs).

The test gel from example 7 was implanted (deposited) into the cavity left by the resection of an EMT-6 ectopic grafted tumor (breast tumor cells) in BALB/cJRj mice.

Just before its implantation, a suspension of hafnium oxide nanoparticles from example 1 was added into the gel via a syringe to reach a final concentration of 0.4% w/w.

The CT analysis was performed 15 minutes (<30 minutes), 2 days and 7 days following gel implantation into the cavity left by the resection of the tumor in order to evaluate the volume occupied by the nanoparticles and/or nanoparticle aggregates in the tumor bed over time. For this, a manual segmentation (region of interest (ROI)) was performed around the surgical cavity. Then a thresholding above 120 HU was performed inside the surgical cavity in order to evaluate the presence of nanoparticles and/or nanoparticle aggregates and to assess both the location and volume occupied by those nanoparticles and/or nanoparticle aggregates for all mice. FIG. 4 presents the CT images showing about 80% cavity delineation as soon as 7 days following surgery and gel implantation.

REFERENCES

Customized Computed Tomography-Based Boost Volumes in Breast-Conserving Therapy: Use of Three-Dimensional Histologic Information for Clinical Target Volume Margins. IJROB 75(3):757-763 (2009).
Target volume definition for external beam partial breast radiotherapy: clinical, pathological and technical studies informing current approaches. Radiotherapy and Oncology 94:255-263 (2010).
Excised and Irradiated Volumes in Relation to the Tumor Size in Breast-Conserving Therapy. Breast Cancer Res Treat 129:857-865 (2011).
Guidelines for target volume definition in post-operative radiotherapy for prostate cancer, on behalf of the EORTC Radiation Oncology Group. Radiotherapy & Oncology 84:121-127 (2007).
Improving the definition of the tumor bed boost with the use of surgical clips and image registration in breast cancer patients. Int J Radiation Oncology Biol Phys 78(5):1352-1355 (2010).
The dynamic tumor bed: volumetric changes in the lumpectomy cavity during breast conserving therapy. Int J Radiation Oncology Biol Phys 74(3):695-701 (2009).

The invention claimed is:
1. A method for delineating and visualizing at least 50% of a tumor bed in a subject, wherein the tumor bed is the tissue covering the cavity obtained following tumor resection in the subject, and wherein the method comprises a step a) of depositing on the tumor bed in the subject a biocompatible gel comprising nanoparticles and/or nanoparticle aggregates wherein: i) the nanoparticles and/or nanoparticles of the aggregate comprise hafnium (IV) oxide ($HfO_2$) or comprise gold and hafnium (IV) oxide ($HfO_2$), each of said nanoparticles and/or said nanoparticle aggregate being covered with a biocompatible coating; ii) the concentration of the nanoparticle and/or nanoparticle aggregates in the biocompatible gel is about or less than 0.5% (w/w); iii) the biocompatible gel comprises cellulose, methylcellulose, carboxymethylcellulose, hydroxymethylcellulose, hydroxyethylcellulose, hydroxypropylcellulose, or hyaluronic acid; and iv) the apparent viscosity at $2\ s^{-1}$ of the biocompatible gel comprising nanoparticles and/or nanoparticle aggregates is between about 1 Pa·s and about 750 Pa·s when measured between 20° C. and 37° C. and the gel is deposited in a layer having a thickness between 100 µm and 0.5 cm, wherein the nanoparticles and/or the nanoparticle aggregates of said gel delineate the tumor bed, and a step b) of visualizing at least 50% of the delineated tumor bed in the subject using X-ray imaging equipment.

2. The method according to claim 1, wherein the concentration of the nanoparticle and/or nanoparticle aggregates in the biocompatible gel is between about 0.15% and about 0.5% (w/w).

3. The method according to claim 1, wherein the nanoparticles and/or nanoparticle aggregates comprise hafnium oxide ($HfO_2$).

4. The method according to claim 1, wherein the nanoparticle or nanoparticle aggregate further comprises at least one targeting agent.

5. The method according to claim 1, wherein the X-ray imaging equipment is a CT scanner.

6. The method according to claim 1, wherein the nanoparticles and/or nanoparticle aggregates comprise hafnium (IV) oxide ($HfO_2$) and gold.

7. The method according to claim 1, comprising delineating and visualizing at least 70% of the tumor bed in the subject.

8. The method according to claim 1, comprising delineating and visualizing at least 80% of the tumor bed in the subject.

9. The method according to claim 1, wherein the step of delineating and visualizing the tumor bed is performed between 24 hours and two weeks after the step of depositing on the tumor bed in the subject the biocompatible gel comprising nanoparticles and/or nanoparticle aggregates.

10. The method according to claim 1, wherein the biocompatible gel is selected from methylcellulose, carboxymethylcellulose, hydroxyethylcellulose and hydroxypropylcellulose.

11. The method according to claim 1, wherein the nanoparticles comprise gold metal covered with hafnium oxide.

* * * * *